Figure 1:
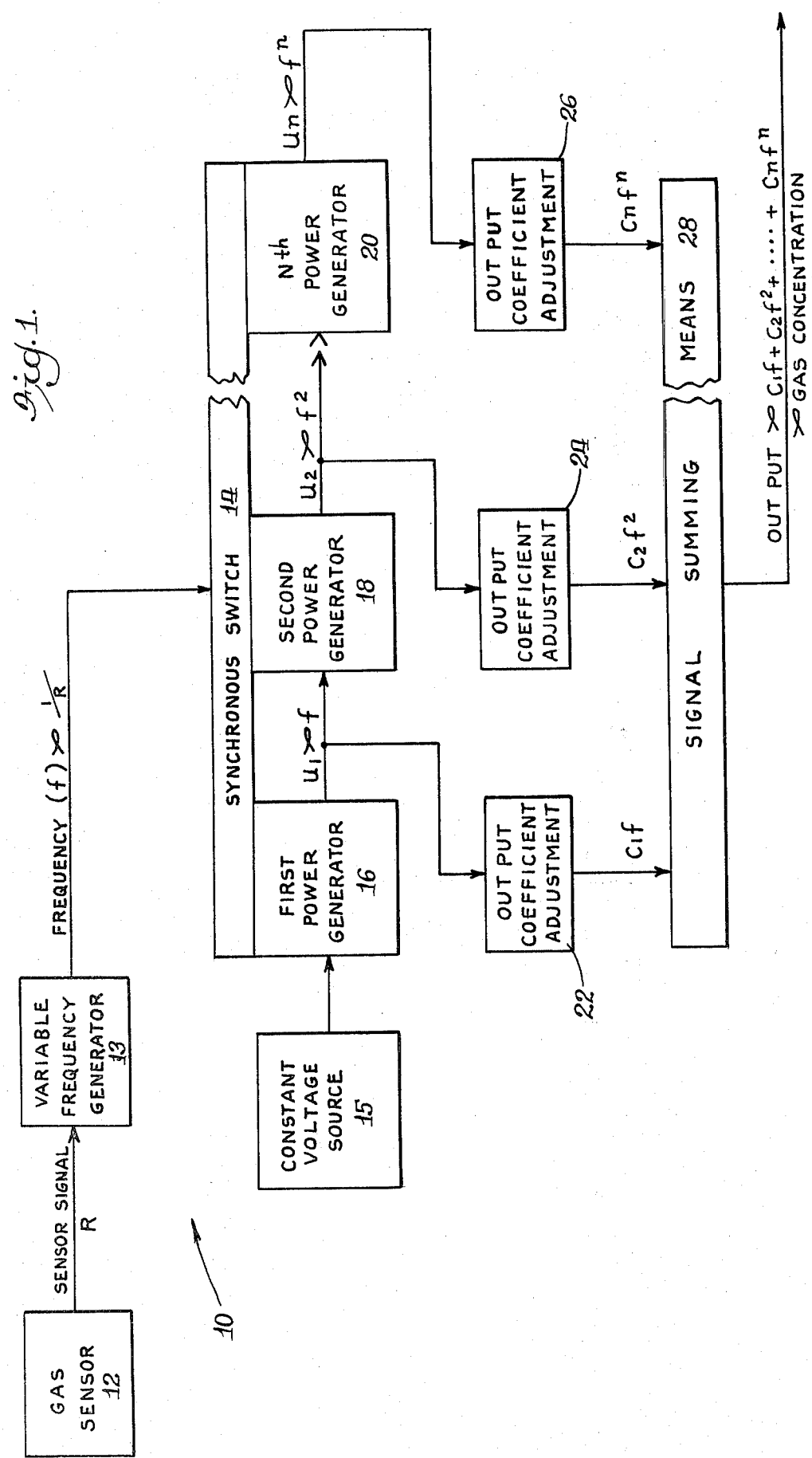

United States Patent [19]

Typpo

[11] 4,432,224
[45] Feb. 21, 1984

[54] HYDROGEN SULFIDE MEASURING SYSTEMS AND THE LIKE

[75] Inventor: Pekka M. Typpo, Cupertino, Calif.

[73] Assignee: Delphian Corporation, Sunnyvale, Calif.

[21] Appl. No.: 369,896

[22] Filed: Apr. 19, 1982

[51] Int. Cl.³ ............................................. G01N 27/12
[52] U.S. Cl. ......................................................... 73/23
[58] Field of Search ................. 73/23, 27 R; 340/632, 340/633, 634; 422/94.98

[56] References Cited

U.S. PATENT DOCUMENTS

| | | | |
|---|---|---|---|
| 4,197,089 | 4/1980 | Willis et al. | 340/634 |
| 4,327,361 | 4/1982 | Berlin | 340/634 |
| 4,351,181 | 9/1982 | Currans | 73/23 |

FOREIGN PATENT DOCUMENTS 3025985  1/1982  Fed. Rep. of Germany .......... 73/23

Primary Examiner—Stephen A. Kreitman
Attorney, Agent, or Firm—Fitch, Even, Tabin & Flannery

[57] ABSTRACT

Methods and apparatus for transforming nonlinear sensor response such as that of a hydrogen sulfide detector to provide a desired output signal as a polynomial signal function.

10 Claims, 2 Drawing Figures

4,432,224

HYDROGEN SULFIDE MEASURING SYSTEMS AND THE LIKE

The present invention is directed to electronic measurement circuitry, and more particularly, is directed to methods and apparatus for providing an output signal as a predetermined polynomial function of the measurement signal of a sensor element such as a detector element which is sensitive to hydrogen sulfide.

Various types of physical sensors, such as hydrogen sulfide gas detection sensor elements which vary in resistance or other measurement signal in response to the presence of the gas to be detected, are conventionally utilized in detection, process control and other measurement applications. However, such resistance variation or other signal response of such sensor elements is unfortunately not necessarily directly proportional to the gas concentration, and requires correction or other signal processing to convert the sensor output signal to a desired output parameter. For example, sensor elements such as conventional detector elements which utilize the variation of electrical resistance of tungsten oxide as a function of hydrogen sulfide concentration have a resistance variation which is a complex function of the hydrogen sulfide concentration. If it is desired to provide an output signal which is directly proportional to the gas concentration, signal correction circuits such as logarithmic amplifiers or anti-logarithmic circuits, which may be relatively complicated, unstable or expensive may be utilized to carry out such conversion. However, improved circuit designs which provide flexible, stable and reliable sensor signal processing would be desirable.

Figure 2:
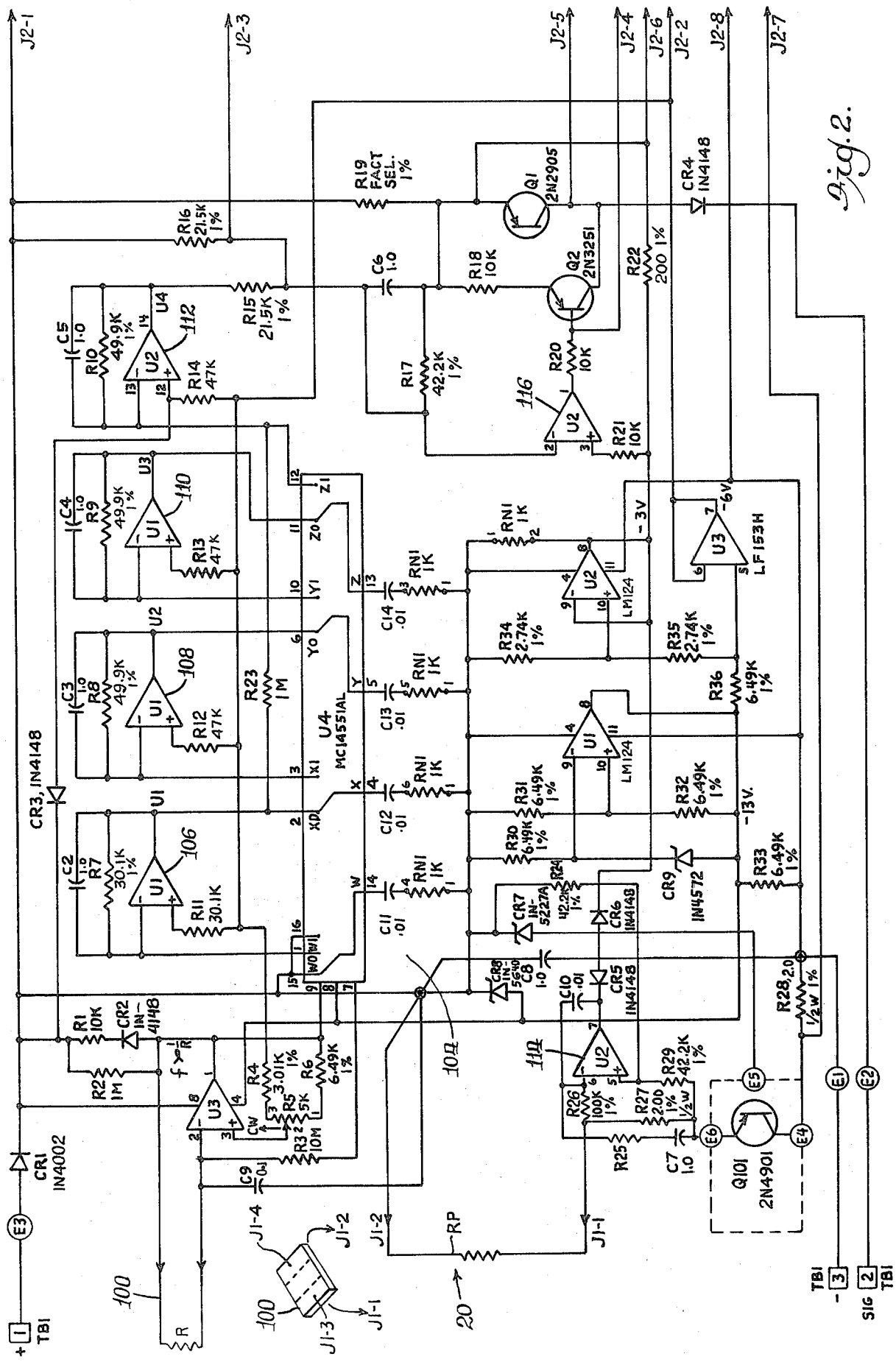

Accordingly, it is an object of the present invention to provide improved methods and apparatus for processing sensor input signals to provide a desired output conversion. These and other objects of the invention will become more apparent from the following detailed description and the accompanying drawings of which:

FIG. 1 is a schematic illustration of a hydrogen sulfide measurement circuit in accordance with the present invention; and FIG. 2 is a schematic illustration of a specific embodiment of a hydrogen sulfide measurement system utilizing various aspects of the present invention.

Generally in accordance with the present invention, methods and apparatus are provided for detecting and measuring a desired physical phenomenon such as a specific gas concentration, in which the detector response is not directly proportional to the quantity desired to be measured.

In accordance with apparatus aspects of the present invention, measurement devices are provided comprising a sensor element which provides an analog output signal responsive to the physical phenomenon desired to be measured, such as hydrogen sulfide concentration. The sensor element may desirably be a sensor element which varies in resistance in response to variations in the external stimulus to which it is sensitive, such as a tungsten oxide film the resistivity of which varies with hydrogen sulfide concentration applied thereto.

The apparatus further comprises variable frequency generator means for receiving the sensor element output signal and generating an output signal having a frequency which is a predetermined function of the sensor output signal. Desirably, this output signal frequency will be substantially directly or inversely proportional to the sensor output parameter proportional to the analog sensor signal. When the sensor element is a variable resistance element such as a tungsten oxide-based detector which decreases in resistivity with increasing concentration of the gas to which it is sensitive, it is desirable that the frequency of the variable frequency generator means be substantially inversely proportional to the variable sensor resistance parameter.

Further in accordance with the present invention, the apparatus comprises power series signal generating means responsive to the output signal of the variable frequency generator means for generating a plurality of output signals respectively proportional to different powers of the frequency of the output signal of the variable frequency generator means. The power series means will desirably provide a plurality of at least three different signals respectively proportional to different integer powers of the frequency generator output signals, and may comprise a plurality of cascaded capacitor charge pump amplifiers as will be more fully described, which are synchronously responsive to the variable frequency generator signal frequency. In certain preferred embodiments, the power series generating means will provide an output signal proportional to the first and fourth powers of frequency.

The measurement apparatus may further comprise means for combining a plurality of the different output signals of the power series means with predetermined respective combination coefficients to provide an output signal having a predetermined functional correlation to the sensor output signal. Preferably, at least two different output signals of the power series means may be combined with appropriate combination coefficients to provide an output signal which is directly proportional to the physical parameters desired to be measured, such as the hydrogen sulfide concentration in the sensor element environment.

In accordance with various method aspects of the present invention, methods are provided for detecting and measuring a desired physical phenomenon such as a specific gas concentration. Such methods comprise sensing the desired physical phenomenon to provide an output signal which is a function of the phenomenon, but which is not only linear responsive thereto. Desirably, the output signal may be a current signal which increases with increasing concentration of a substance which is to be detected such as provided by the current provided through a sensing element which decreases in electrical resistance as a function of increasing hydrogen sulfide concentration. The method further contemplates generating a variable frequency signal having a frequency which is a predetermined function of the sensor output signal. Desirably, the output signal frequency will be substantially directly or inversely proportional to the sensor output signal parameter. Further in accordance with the method, a plurality of signals are generated which are respectively proportional to different powers of the frequency of the variable frequency signal. These output signals will desirably comprise a plurality of at least three different signals which are respectively proportional to different integer powers of the variable frequency signal. Such signals may desirably be provided by pumping a predetermined charge quantity at said variable frequency to provide a first output signal directly proportional to the variable frequency, pumping a charge quantity proportional to said first output signal at said variable frequency to provide an ouput signal proportional to the variable frequency, and similarly pumping additional charge quantities proportional to respective frequency powers at the variable frequency to provide higher order signals. Further in accordance with such methods, a plurality of different output signals are combined with predetermined respective combination coefficients to provide an output measurement signal having a predetermined functional correlation to the sensor output signal.

Illustrated in FIG. 1 is a schematic diagram illustrating in block form a measurement system 10 which comprises a sensor element 12 which is responsive to a selected external stimulus; the element 12 may be a heated tungsten oxide hydrogen sulfide detector element which decreases in resistance in response to an increasing concentration of hydrogen sulfide surrounding the active portion of the sensor element 12.

The sensor element 12 provides an input signal R, which in the illustrated embodiment represents the variable resistance of the sensor element 12, to a variable frequency generator 13. The variable frequency generator 13 is adapted to provide an output signal which varies in frequency as a function of the input signal, and in the illustrated embodiment 10, the frequency of the output signal of the variable frequency generator 13 is inversely proportional to the sensor output parameter R, which for the sensor 12 represents the resistance of the sensor element. The resistance of the element 12 will decrease with increasing hydrogen sulfide concentration in the sensor environment, but not in a manner which is directly inversely proportional to concentration. The generator 13 may conveniently be a RC-relaxation oscillator circuit, and the sensor 12 may conveniently form a variable resistance element of this RC-relaxation oscillator to provide the variable frequency output signal. The variable frequency output, which is proportional to the sensor input parameter, is utilized as an input signal to a synchronous switch 14 for a plurality of power series generator circuits 16, 18 . . . 20, which are adapted to provide output signals proportional to increasing integer powers of the frequency of the output signal of the variable frequency generator 13. In this regard, the first power generator 16 and the switch 14 pump a predetermined quantity of electrical charge proportional to a fixed input potential supplied by constant voltage source 15, at the frequency (f) of the generator 13. This provides an output current directly proportional to the frequency (f), which is translated by appropriate means to a potential signal U1 which is similarly directly proportional to the frequency (f) of the variable frequency generator 13. The second power generator 18 together with the synchronous switch 14, receives the signal U1 and pumps a predetermined quantity of charge proportional to the potential of signal U1, at the frequency (f) to produce an output signal U2. Because the potential of signal U1 is proportional to the frequency (f), which in turn is "pumped" at frequency (f), the output signal U2 is proportional to the square of the frequency (f) of the generator 13.

A plurality of such cascaded power series generator circuits may be provided, which in the illustration of FIG. 1 are shown by breaking the illustration at the second power generator 18, and terminating in an Nth power generator 20 which receives an input signal U(n−1) from a preceding power generator having a potential proportional to the n−1 power of the frequency (f). Upon pumping charge quantities proportional to the potential of signal U(n−1) at a frequency (f), an output signal Un is generated which is proportional to the nth power of the frequency (f). The various output signals of the generators 16, 18 . . . 20 may be subjected to appropriate relative proportional adjustment by respective circuit elements 22, 24, . . . 26, which may readily be carried out by appropriate resistance elements or gain factors of the enabling circuitry. In this regard, the output signal U1 of the first power generator 16 may have a proportioning coefficient applied thereto such that an output signal proportional to C1 and the first power of the frequency (f) is provided. Similarly, the output signal U2 of the second power generator 18 may have a proportioning coefficient applied thereto to provide an output signal proportional to coefficient C2 and the second power of the frequency (f). Similarly the nth power output signal of generator 20 may have a selected proportioning coefficient applied thereto to provide an nth power frequency output signal with a proportioning coefficient Cn. These respective, proportional signals may be summed by appropriate signal summing means 28 which provides an output signal in a desired polynomial relationship in respect to the frequency of the input signal f.

The combination of proportional signal components shown schematically may also be carried out by combining the appropriate signals U1, U2, etc. from a lower order generator, directly as input signal component(s) to the respective power generators to provide respective output signals which are proportional to additional powers of frequency (f), as will be more fully described hereinafter. The predetermined polynominal relationship may be selected to correspond to an empirically determined relationship between the sensor response, and the desired quantity which is being measured, such as the actual hydrogen sulfide concentration.

Turning now to FIG. 2, various aspects of the present invention will now be more particularly described with respect to the embodiment 20 of hydrogen sulfide measurement apparatus there shown in detailed schematic representation of the various circuit components.

Tungsten oxide hydrogen sulfide detection element 100 such as device PN 7000 supplied by Delta Safety Systems of California, comprises a tungsten oxide layer on one side of a ceramic substrate, with a platinum heater element on the other side of the substrate to permit heating of the tungsten oxide to an elevated temperature as indicated by the figure insert. The illustrated tungsten oxide sensor element has a conductance which varies predominantly in a first order and fourth order function of hydrogen sulfide concentration, such that its output cannot be directly accurately converted to hydrogen sulfide concentration over a broad concentration range without signal manipulation. The tungsten oxide film is represented in the schematic diagram of FIG. 2 by variable resistance element 12 which makes electrical connection with relaxation oscillator circuit by means of pin connectors J1-3 and J1-4. The tungsten oxide sensor film is maintained at a constant elevated temperature by the platinum heater element, which is represented in the schematic by resistance Rp, which makes connection to a heating circuit by connectors J1-1 and J1-2. When there is no hydrogen sulfide present at the sensor 100, the resistance R of the tungsten oxide film has a very high impedance on the order of from about one hundred kilohms or more to ten megaohms or more. The sensor resistance element R is part of a relaxation oscillator 102 comprising differential amplifier U3, pins 1, 2, 3, resistors R3, R4, R5, R6 and capacitor C9. The frequency of the oscillator 102 is determined by the oxide resistance and capacitor C9. Because the capacitance of C9 is constant, the output frequency of the oscillator 102 is directly proportional to the conductance, and inversely proportional to the resistance R of the tungsten oxide film of the sensor, multiplied by the log of a resistance expression determined by resistors R4, R5, R6. This frequency response constant of the oscillator 102 may be adjusted by variable resistor R5. When the sensor 100 is exposed to hydrogen sulfide gas, there is a dramatic decrease in the resistance of the sensor. In this regard, a typical impedance R of the tungsten oxide sensor film at, for example, about 100 parts per million by volume of hydrogen sulfide is from about 2 to about 2.5 thousand ohms. Therefore, the relaxation oscillator frequency, which is inversely proportional to the sensor resistance will increase. The frequency of the oscillator 102 is accordingly substantially inversely proportional to sensor resistance R, and the dependence between hydrogen sulfide concentration and for the indicated sensor 100, this frequency is primarily a fourth power relationship of the hydrogen sulfide concentration, with correction term of first power.

The output signal at frequency (f), which is inversely proportional to sensor resistance R and which will vary as the hydrogen sulfide concentration of the sensor varies, is provided at output pin 1 of differential amplifier U3, pins 1, 2, 3. The output forms an input to pin 9 of a switching element U4, pins 1 through 16 to drive an array of switched capacitor banks, as will now be described. The switch U4 comprises four synchronously operating switch elements W, X, Y and Z, which operate at the variable frequency (f) of the oscillator 102. U4 subswitch W alternately and synchronously with the other subswitches connects position W of pin 14 with position W0 of pin 15 and position W1 of pin 16. U4 subswitch X alternately connects position X of pin 4 with position X0 of pin 2 and position X1 of pin 3. Similarly, U4 subswitch Y alternately connects position Y of pin 5 with position Y0 of pin 6 and position Y1 of pin 10. Likewise, U4 subswitch Z alternately connects position Z of pin 13 with positions Z0 of pin 11 and position Z1 of pin 12 at the cycle frequency of (f).

Device U4 subswitch W controls the operation of the first power switched capacitor stage 106, which comprises differential amplifier U1, pins 1, 2, 3, capacitor C2, C11 and resistors R7, R11 and RN1. In the operation of first power stage 106, a predetermined amount of charge is pumped at the frequency (f) to provide an output signal which is translated to an appropriate potential proportional to the first power of the oscillator frequency (f). The amount of charge which is pumped is proportional to a 6 volt constant voltage reference potential, which is applied to charge capacitor C11 to such voltage when the switch W of device U4 is in position W0 for half of the switch cycle. The switch connects capacitor C11 at position W to position W1 and discharges capacitor C11 into the summing point, pin 2 of differential amplifier U1, pins 1, 2, 3. Device U1, pins 1, 2, 3 also form a low pass filter with capacitor C2 and resistor R7 determining the time constant. The time constant is such, and the relationship between C11 and C2 is such, that the operational frequency (f) is filtered, and a potential having a low ripple is provided at the output pin 1 of device U1, pins 1, 2, 3. The output potential at pin 1 of device U1, pins 1, 2, 3 is accordingly substantially proportional to the average current that goes into the summing point 2. In the illustrated embodiment 20, operational frequency (f) may range from about 1-2 kilohertz at maximum scale hydrogen sulfide concentration (e.g., 100 parts per million), to a frequency (f) for example of about 0.1 Hz at the maximum device impedance in the absence of hydrogen sulfide. The illustrated first stage 106 has a time constant of 30 milliseconds, which is adequate to provide a low ripple output potential for first power generator 106. The charge ratio of the capacitors C11 and C2 determines step ratio upon discharge, which in the illustrated embodiment is a ratio of 100 to one, provides additional control in the translation of the pumped current to an output potential proportional to the first power of frequency (f). Accordingly, it will be appreciated that an output signal U1, which is inverted by the differential amplifier of stage 106, is provided at pin 1 of first power generator stage 106 according to the relationship:

$$-U1 = f*C11*R7*6 \text{ volts} \tag{1}$$

This signal is applied to the second power generator stage 108 so that charge quantities proportional to this signal, rather than fixed charge quantities proportional to the fixed 6 volt reference potential supplied to the preceeding circuit 106, are pumped at frequency (f) by operation of the circuit 108. The second power circuit 108 is similar to the preceeding circuit 106, and comprises operational amplifier U1, pins 5, 6, 7, capacitors C3, C12, subswitch X of device U4 and resistors R8, R12 and RN1. The circuit 108 has a different filter time constant, but is otherwise similar to first power stage 106. The input potential, however, as indicated now comes from the previous stage 106. In operation, subswitch X charges capacitor C12 for one half cycle, and then discharges to summing point pin 6 of operational amplifier U1 pins 5, 6, 7. The output potential at pin 7 of that amplifier is accordingly represented by a signal U2 which is proportional to the second power of the frequency (f), again inverted in sign by the amplifier circuit, as follows:

$$-U2 = f*C12*R8*U1 \tag{2}$$

Therefore, the output is substantially proportional to the second power of the frequency of the relaxation oscillator 102. The output signal U2 is similarly applied to control the quantity of charge pumped by third power stage 110, comprising differential amplifier U1, pins 12, 13, 14, capacitor C4, C13, resistors R9, R13 and RN1, and subswitch Y of device U4, which is substantially identical to the second power stage 108. The third power stage generator 110 synchronously charges capacitor C13 to potential U2 and subsequently discharges its summing node at frequency (f). The output signal U3, similarly inverted in sign, is accordingly provided at pin 14 of operational amplifier U2 pins 12, 13, 14 according to the following relationship:

$$-U3 = f*C13*R9*U2 \tag{3}$$

The fourth power stage 112 comprises device U2, pins 12, 13, 14, capacitors C5, C14, subswitch Z and resistors R10, R14, RN1. The output signal U3 of third power generator 112 controls the quantity of charge pumped, as previously described in respect to generators 108, 110. In the absence of resistor R23, the output of stage 112 would be a substantially proportional fourth power of the conductivity of sensor device 100. However, resistor R23 is provided to couple the first stage output to the last stage 112 summing point to provide an additional term to the final stage that is proportional to the first power of the frequency. Accordingly, the output, at pin 14 of the amplifier U2 of fourth power generator 112 is proportional to a polynomial which consists of fourth power and first power terms, the fourth power term dominates at higher hydrogen sulfide concentrations at a level which may be selected by adjusting the value of R23.

The synchronous operation of switch U4 at frequency (f) is an important feature of circuit 20. The switch U4 is a CMOS switch with a single input control at pin 9, which selects whether all the subswitches W, X, Y and Z are either in position zero or position one. In position zero, the capacitors on pins 14, 5, 13 and 4 are charged with the current limiting resistor network RN1, to the fixed six volt input potential (for first stage 106) or the respective output potential of the previous stage. When the switch is changed into position 1, all four switches transfer respectively the charges controlled thereby into the next summing input of the subsequent stage. This switch is driven at the frequency of the output of the relaxation oscillator circuit 102, as previously indicated, so that the power factor in terms of frequency (f) is increased at each cascaded stage.

As indicated, the tungsten oxide film of sensor 100 is heated to an elevated temperature, which may, for example, be maintained at about 200° C. by heater control circuit 114 comprising amplifier U2, pins 5, 6, 7, as shown in FIG. 2. The heater element Rp is a platinum resistor of the sensor 100 which forms part of a resistance bridge comprising the heater itself and resistors R27, R29 and R24.

The temperature control circuit functions to maintain a constant temperature. Transistor Q101 (2N4901) adjusts the overall bridge voltage in such a way that when the heater circuit increases from an ambient temperature resistance of about 11–12 ohms to increase the platinum element resistance Rp to a selective resistance of, say 20 ohms at the desired operating temperature.

Resistors R25, R26 capacitors C7 and C10 are feedback circuit elements to maintain the heater at a constant resistance, and therefore, at constant temperature. The output of heater circuit 114 is clamped with diode CR7 to prevent it from accidently exceeding the heater current capability, and diode CR6 is tied to a 3 volt reference to insure that amplifier U2 is brought at start up to its proper common mode range.

Amplifiers U1, pins 8, 9, 10, U2 pins 8, 9, 10, and U3, pins 5, 6, 7 and associated circuit elements as shown FIG. 2 provide various internal voltage references. The circuitry provides a minus 13 volt voltage reference to be used for the CMOS chip U4 and amplifier U3, of the relaxation oscillator, so that the frequency of oscillator 102 will not be dependent upon voltage variations. The total voltage across the circuit 20 can vary from, say, 14 volts up to about 30 volts, and then these reference circuits are referenced to the high voltage, with the minus side being permitted to float freely to facilitate operation of the current output stage 116 of the device 20 which comprises amplifier U2, pins 1, 2, 3 and transistors Q1 and Q2.

In the illustrated device 20, the output signal U4 is translated into a current signal which may be transmitted over a suitable transmission line to a remote station without signal loss. To carry out the potential to current translation, the potential U4 at amplifier U2, pins 14 of stage 112 is directed to resistor R15 of the summing point of the final current output stage 116. The output current is selectable to provide a range, for example, of either 4 to 20 milliamps or 1 to 5 milliamps, by resistor R19, to determine the output current where there is not input at zero hydrogen sulfide concentration. When hydrogen sulfide is detected, the output current may be chosen by changing resistor R22.

The output signal of the output stage 116 is a current signal which is substantially linearly proportional to hydrogen sulfide concentration plus a selectable current offset. In the illustrated embodiment, the output current Iout provided by circuit 116 may be represented as:

$$\text{Iout} = [U4 * R17 / R15 * R22] + 3 \text{ volts} / R19 \tag{4}$$

External power to the circuit 20, which nominally may be about 24 volts (e.g., 19 to 30 volts) is provided across terminal TB1-1 and TB1-3 as indicated in FIG. 2, with the output current signal being provided to terminal TB2-2.

An additional feature of the circuit 20 is an open circuit detector 120 comprising diode CR2, resistors R1, R2 and capacitor C1, which distinguishes an open circuit such as represented by a faulty sensor 100, and the higher impedance of the detector at zero hydrogen sulfide concentration. Resistor R3 provides a comparison so that if the RC circuit opens us, amplifier U3 will be low if it stops. If it were to stop high, there would be no alarm. When it stops low, then resistor R2 will showly discharge capacitor C1. When that happens, diode CR3 will pull pin 12 of operational amplifier U2 down, and therefore, create a negative signal at the output of fourth powers stage 112 while the oscillator 102 is operating properly, diode CR3 keeps C1 charged through resistor Rl. Therefore diode, CR3 is reverse biased, and does not normally affect device U2, pin 12, except in the case of an open circuit.

While the illustrated embodiment 20 provides an output signal consisting essentially of only first and fourth power terms required to convert the particular sensor response to hydrogen sulfide to an accurate output signal representative of concentration of hydrogen sulfide at the sensor, it will be appreciated that other polynomial output signals may be readily provided for other sensors or signal processing requirements. In this regard, there is an inverting stage after the fourth power stage 112 so that two summing points are provided having negative and positive summing points to create any fourth power polynomial desired by directly applying the appropriate power term to the appropriate inputs of the device U2, pins 1, 2, 3.

Alternatively, as carried out in embodiment 20, in part, first power, second power and third power outputs, which are alternately inverted with respect to each other may be applied to the appropriate one of the two summing nodes of the operational amplifier U2, pins 12, 13, 14 of final state 112.

Furthermore, additional, or fewer, power generator stages may be utilized to achieve a desired polynomial output. In addition, while the illustrated embodiment utilizes only one sensor element, a plurality of sensor elements differently responsive to one or more substances may be provided with respectively associated oscillators and power series generators, to produce respective power series which may be appropriately processed to provide increased measurement accuracy or measurements of different substances which affect sensors in different degrees.

While the present invention has been particularly described with respect to a specific embodiment, it will be appreciated that various modifications, adaptations and variations will become apparent based on the present disclosure, which are intended to be within the spirit and scope of the present invention.

Various of the features of the invention are set forth in the following claims.

What is claimed is:

1. Apparatus for detecting and measuring a physical phenomenon such as a gas concentration or the like, comprising a sensor element which provides an analog output signal responsive to the physical phenomenon desired to be measured, variable frequency generator means for receiving the sensor element output signal and generating an output signal having a frequency which is a predetermined function of the sensor output signal, power series signal generating means responsive to the output signal of the variable frequency generator means for generating a plurality of output signals respectively proportional to different powers of the frequency of the output signal of the variable frequency generator means, and combining means for providing a combined plurality of the different output signals of the power series signal generating means having predetermined respective combination coefficients to provide an output signal having a predetermined functional correlation to the sensor output signal.

2. A measurement device in accordance with claim 1 wherein said sensor element is a hydrogen sulfide sensor element which varies in resistance as a nonlinear function of hydrogen sulfide concentration.

3. A device in accordance with claim 2 wherein said variable frequency generator means provides an output signal directly proportional to the conductivity of the sensor element.

4. A device in accordance with claim 3 wherein at least two of said different power series signals are combined to provide an output measurement signal linearly responsive to hydrogen sulfide concentration.

5. A device in accordance with claim 4 wherein said output measurement signal consists substantially of first and fourth order terms.

6. A device in accordance with claim 5 wherein said measurement output signal is an output potential signal.

7. A device in accordance with claim 5 wherein said measurement output signal is a current signal including an offset current component.

8. A method for detecting and measuring selected gas concentration comprising the steps of sensing the gas concentration to provide an output signal which is a nonlinear function of the gas concentration, generating a variable frequency signal having a frequency which is a predetermined function of the sensor output signal, generating a plurality of signals which are respectively proportional to different powers of the frequency of the variable frequency signal, and combining a plurality of said different output signals with predetermined respective combination coefficients to provide an output signal having a predetermined functional correlation to the sensor signal.

9. A method in accordance with claim 8 wherein a first power signal is generated by pumping a predetermined charge quantity at said frequency to provide a first power signal directly proportional to the variable frequency, pumping a charge quantity proportional to said first output signal at said variable frequency to provide an output signal proportional to the variable frequency, and similarly pumping at least one additional charge quantity proportional to respective frequency powers at the variable frequency to provide higher order signals.

10. A method in accordance with claim 8 wherein at least one of said plurality of signals is proportional to a plurality of integer powers of said frequency.

* * * * *